(12) United States Patent
Su et al.

(10) Patent No.: US 8,658,658 B2
(45) Date of Patent: Feb. 25, 2014

(54) COMPOUND, CERTAIN NOVEL FORMS THEREOF, PHARMACEUTICAL COMPOSITIONS THEREOF AND METHODS FOR PREPARATION AND USE

(75) Inventors: Wei-Guo Su, Shanghai (CN); Weihan Zhang, Shanghai (CN); Hong Jia, Shanghai (CN); Yumin Cui, Shanghai (CN); Yongxin Ren, Shanghai (CN); Yang Sai, Shanghai (CN); Zhenping Wu, Shanghai (CN); Wenji Li, Shanghai (CN); Jiangyong Shao, Shanghai (CN); Zhenping Tian, Shanghai (CN)

(73) Assignee: Hutchison MediPharma Limited, Shanghai (CN)

( * ) Notice: Subject to any disclaimer, the term of this patent is extended or adjusted under 35 U.S.C. 154(b) by 20 days.

(21) Appl. No.: 13/510,249

(22) PCT Filed: Nov. 23, 2010

(86) PCT No.: PCT/CN2010/078997
§ 371 (c)(1),
(2), (4) Date: Jul. 5, 2012

(87) PCT Pub. No.: WO2011/060746
PCT Pub. Date: May 26, 2011

(65) Prior Publication Data
US 2012/0270889 A1  Oct. 25, 2012

(30) Foreign Application Priority Data
Nov. 23, 2009  (CN) .......................... 2009 1 0199259

(51) Int. Cl.
*A01N 43/54* (2006.01)
*A61K 31/505* (2006.01)

(52) U.S. Cl.
USPC .......................................... 514/272; 544/321

(58) Field of Classification Search
USPC .......................................... 514/272; 544/321
See application file for complete search history.

(56) References Cited

U.S. PATENT DOCUMENTS

2008/0255172 A1* 10/2008 Su et al. ........................ 514/275
2013/0065890 A1*  3/2013 Su et al. ..................... 514/228.2

FOREIGN PATENT DOCUMENTS

| CN | 101289444 A | 10/2008 |
| WO | WO 2007/035309 A1 | 3/2007 |
| WO | WO 2008/128231 A1 | 10/2008 |
| WO | WO 2010/025138 A2 | 3/2010 |

OTHER PUBLICATIONS

Extended European Search Report dated Mar. 15, 2013, issued from the European Patent Office for European Patent Application No. 10831161.4.
International Search Report, dated Mar. 3, 2011, issued in PCT/CN2010/078997.

* cited by examiner

*Primary Examiner* — James O Wilson
*Assistant Examiner* — Alexander R Pagano
(74) *Attorney, Agent, or Firm* — Finnegan, Henderson, Farabow, Garrett & Dunner, LLP

(57) ABSTRACT

Compound of Formula A and pharmaceutically acceptable salts thereof and crystalline Forms I and II of Compound of Formula A! Also, methods for the preparation of such compounds, pharmaceutical compositions comprising such compounds, and methods for their uses.

26 Claims, 5 Drawing Sheets

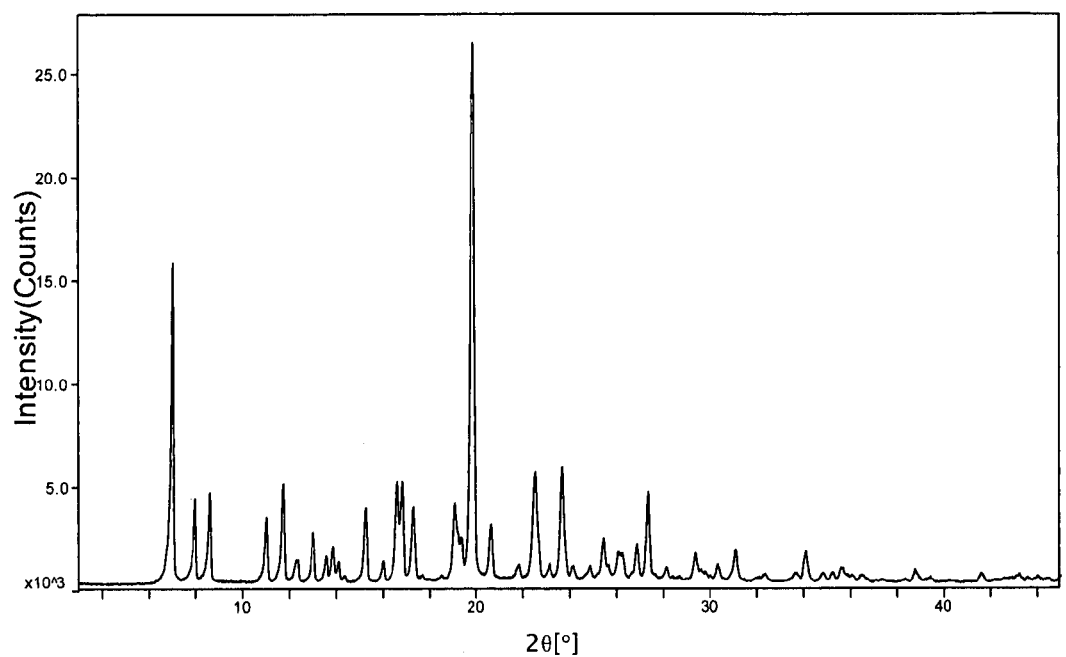
Figure 1: XRPD of Form I

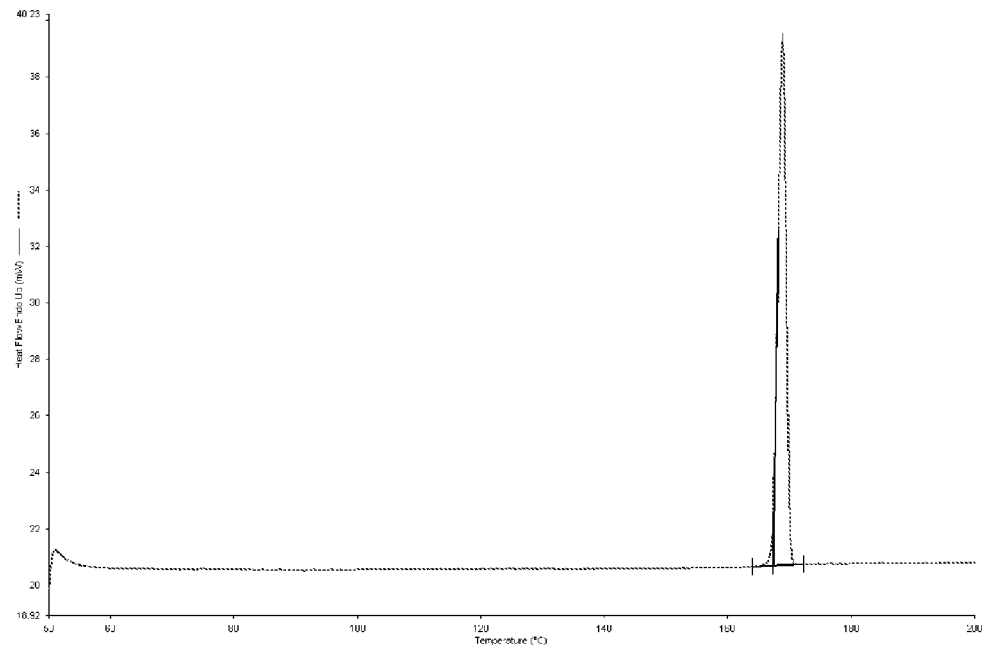
Figure 2: Differential Scanning Calorimeter (DSC) Thermogram of Form I
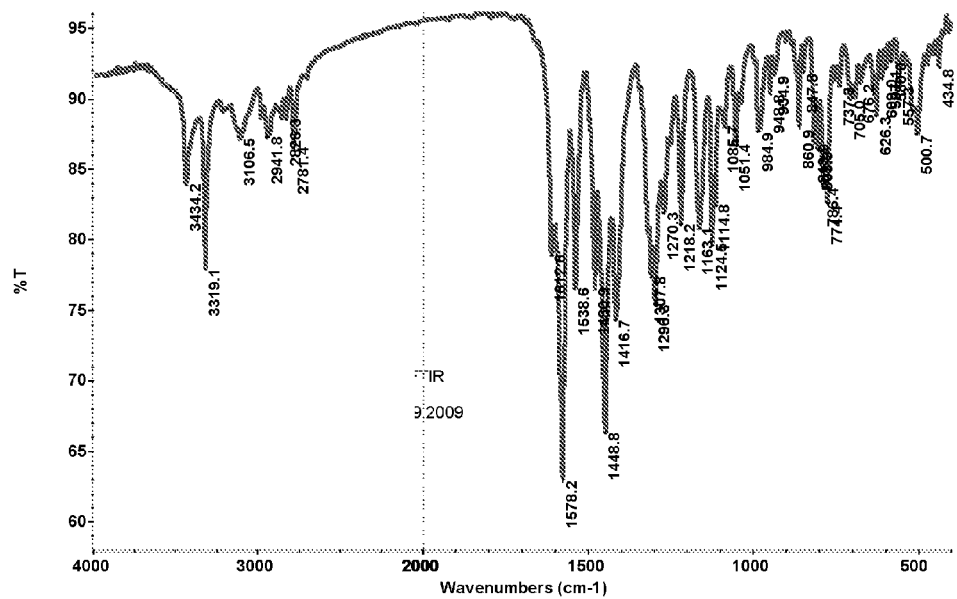
Figure 3: Fourier Transform-Infrared (FT-IR) Spectrum of Form I

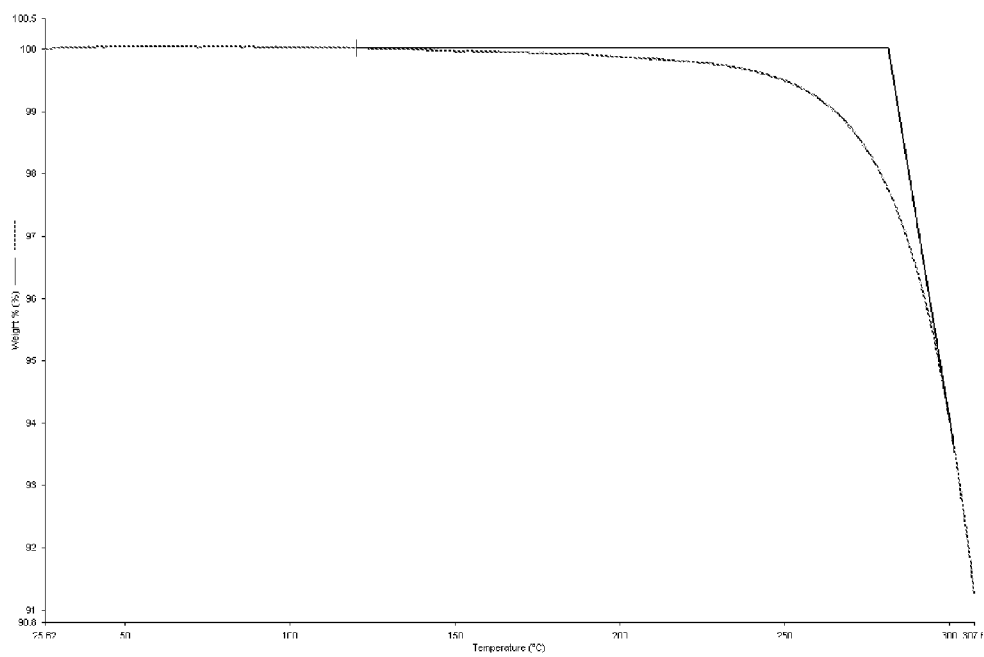
Figure 4: Thermogravimetric (TG) Curve of Form I

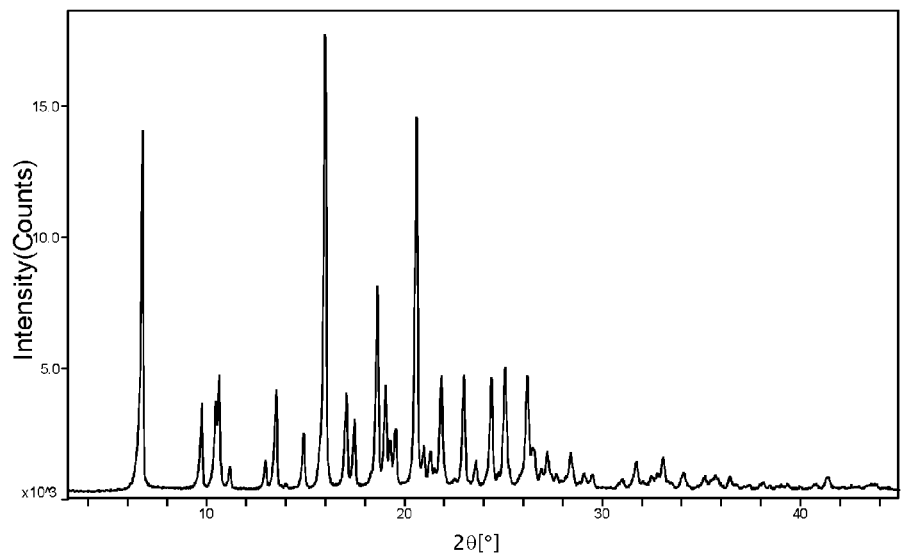
Figure 5: XRPD of Form II
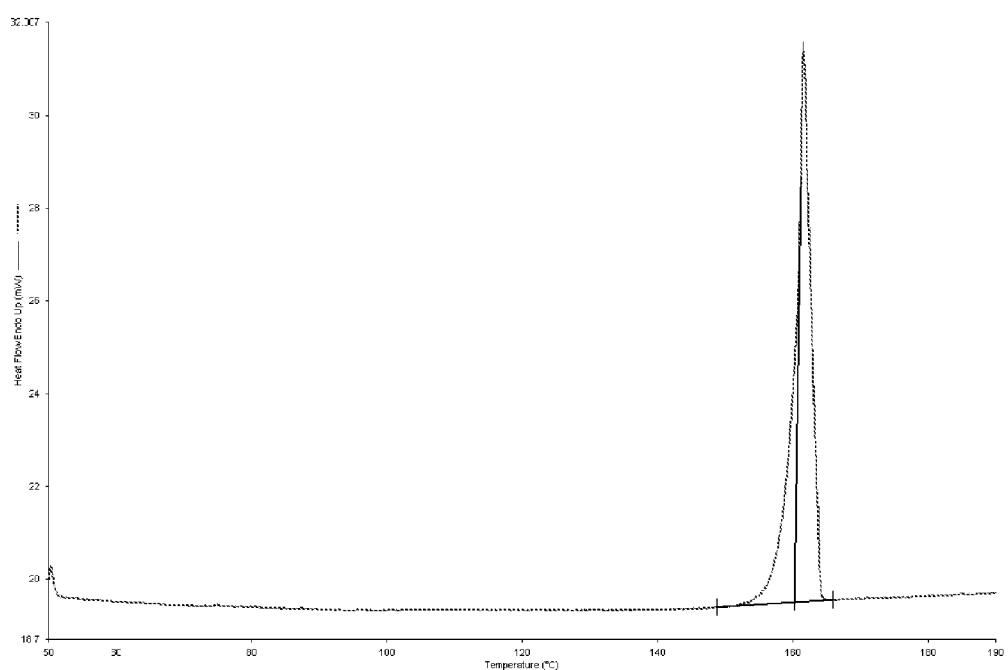
Figure 6: Differential Scanning Calorimeter (DSC) Thermogram of Form II

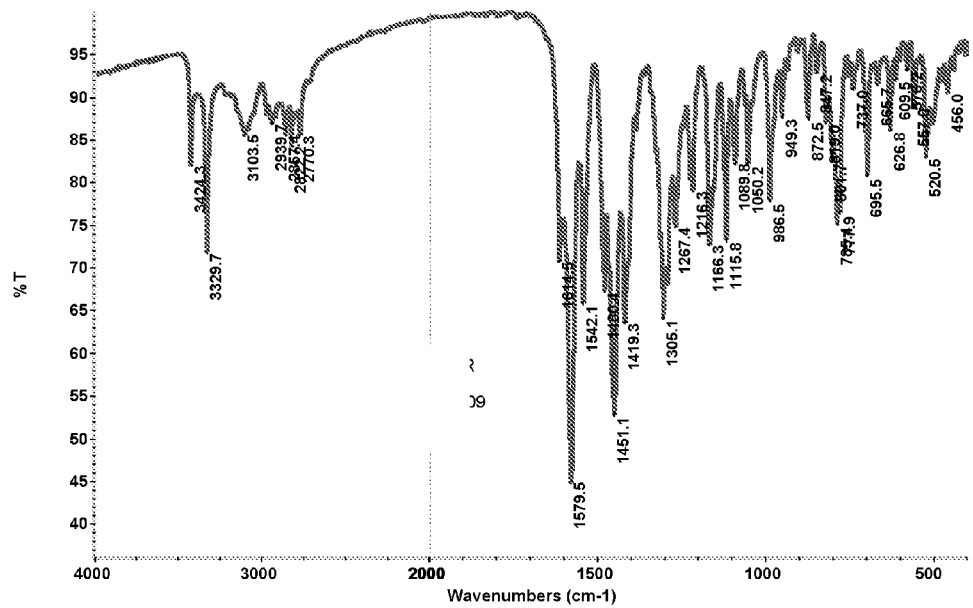
Figure 7: Fourier Transform-Infrared (FT-IR) Spectrum of Form II
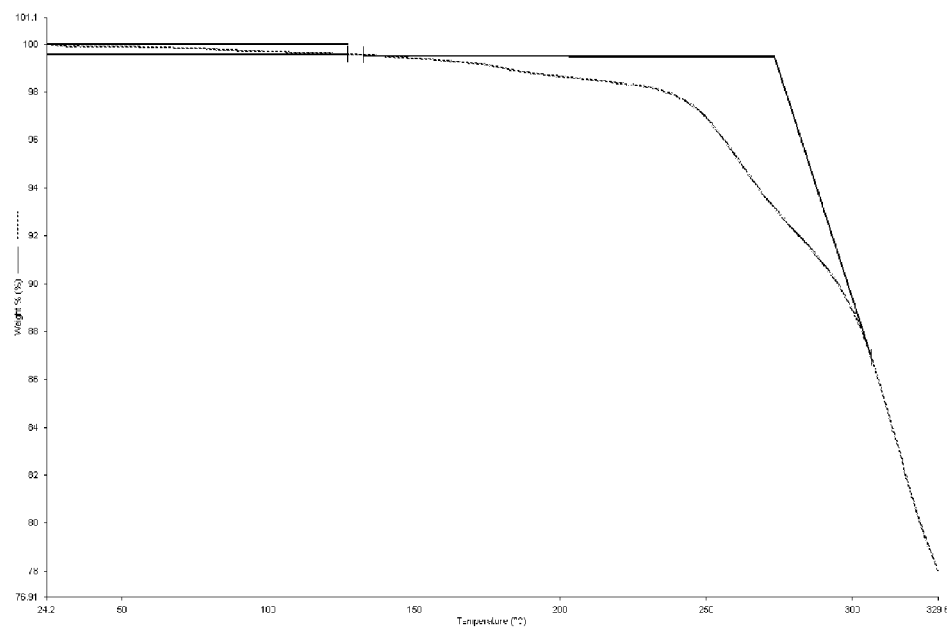
Figure 8: Thermogravimetric (TG) Curve of Form II

COMPOUND, CERTAIN NOVEL FORMS THEREOF, PHARMACEUTICAL COMPOSITIONS THEREOF AND METHODS FOR PREPARATION AND USE

This application is a U.S. national stage entry of International Patent Application No. PCT/CN2010/078997, filed Nov. 23, 2010, which claims priority to Chinese Patent Application No. 2009/10199259 filed Nov. 23, 2009.

Angiogenesis is a process wherein new blood vessels can grow from existing vasculature. That process can occur in wound healing of the body, such as the restoration of blood flow in tissue injury, for example, an injury of the hand. Excess angiogenesis, however, might be initiated under specific pathological conditions, for example tumor, AMD (age-related macular degeneration), rheumatoid arthritis, psoriasis, etc. Under such circumstances, new blood vessels may undesirably tend to provide pathological tissues with nutrition and injure the normal tissues. For example, cancer cells may enter into blood circulation through new blood vessels and invade normal tissues.

VEGF (Vascular Endothelial Growth Factor) and its receptor VEGFR-2 (also called KDR, kinase insert domain-containing receptor) can form the major pathway for the formation of new blood vessels. It has been indicated that inhibition of KDR can cause apoptosis of endothelial cells, which consequently block the angiogenesis process (Rubin M. Tuder, Chest, 2000; 117:281). Thus, KDR inhibitors can be used for the treatment of angiogenesis-related diseases.

FGF (Fibroblast Growth Factor) is a pro-angiogenesis molecule as is VEGF. During angiogenesis, VEGF is thought to be critical in the neovascularization process, and the FGF (Fibroblast Growth Factor)/FGFR (Fibroblast Growth Factor Receptor) axis plays roles in functionally maturing newly formed vessels. In addition, aberrant activation of FGF family members and their cognate receptors have been found in multiple cancers, such as breast, bladder and prostate cancers. FGFR1 and its binding partners FGF1, FGF2, FGF8b and FGF17 are also elevated. In other tumor types, FGFR1 is implicated as an oncogene whose expression is increased compared with normal tissue. Therefore, blockade of FGF/FGFR signaling may be beneficial for treatment of cancers associated with FGF/FGFR activation.

Disclosed herein is a compound of Formula A, e.g., N-(2-(dimethylamino)ethyl)-1-(3-((4-((2-methyl-1H-indol-5-yl)oxy)pyrimidin-2-yl)amino)phenyl)-methanesulfonamide, and/or a pharmaceutically acceptable salt thereof.

disease responsive to KDR inhibition, such as angiogenesis-related disorders, comprising administering to said subject in need thereof an effective amount of the compound of Formula A and/or a pharmaceutically acceptable salt thereof.

Solid-state crystalline forms I and II of the compound of Formula A have been discovered and are disclosed herein. The ability of a compound to exist in more than one crystal structure or form is known as polymorphism. Many compounds may exist unexpectedly as polymorph crystals and those compounds may also exist in a solid amorphous state. Until polymorphism is discovered, it is highly unpredictable (1) whether a particular compound will exhibit polymorphism, (2) how to make any such unknown polymorphs, and (3) what the properties, such as stability, will be of any such unknown polymorphs. See, e.g., J. Bernstein "Polymorphism in Molecular Crystals", Oxford University Press, (2002).

Because the properties of any solid material depend on the structure as well as on the nature of the compound itself, different solid state forms of a compound can and often do exhibit different physical and chemical properties. Differences in chemical properties can be determined through a variety of analytical techniques to be used to characterize, analyze, and compare. And those differences in chemical properties may ultimately be used to differentiate among different solid state forms that may be discovered to exist. Furthermore, differences in physical properties, such as solubility or bioavailability, of solid sate forms can be important when formulating a pharmaceutical compound. As such, novel crystalline and amorphous solid state forms of pharmaceutically useful compounds, such as the compound of Formula A, can be important in the development of such useful compounds.

Also disclosed herein is a novel form of the compound of Formula A, designated Form I N-(2-(dimethylamino)ethyl)-1-(3-((4-((2-methyl-1H-indol-5-yl)oxy)pyrimidin-2-yl)amino)phenyl)-methanesulfonamide.

Also disclosed herein are methods of preparing Form I N-(2-(dimethylamino)ethyl)-1-(3-((4-((2-methyl-1H-indol-5-yl)oxy)pyrimidin-2-yl)amino)phenyl)methanesulfonamide.

Also disclosed herein is a pharmaceutical composition, comprising at least one pharmaceutically acceptable carrier and Form I N-(2-(dimethylamino) ethyl)-1-(3-((4-((2-methyl-1H-indol-5-yl)oxy)pyrimidin-2-yl)amino)phenyl)-methanesulfonamide.

Also disclosed herein is a method of treating a subject in recognized need of treatment for at least one disease respon- Formula A

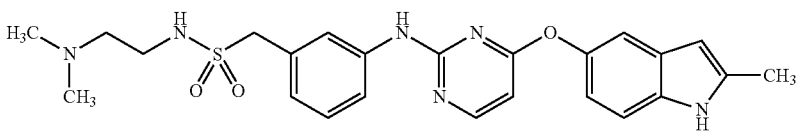

N-(2-(dimethylamino)ethyl)-1-(3-((4-((2-methyl-1H-indol-5-yl)oxy)pyrimidin-2-yl)amino)phenyl)-methanesulfonamide Also disclosed herein is a pharmaceutical composition, comprising at least one pharmaceutically acceptable carrier and the compound of formula A, and/or at least one pharmaceutically acceptable salt thereof.

Also disclosed herein is a method of treating a subject in recognized need of treatment for at least one disease responsive to FGFR1 inhibition, such as cancer, and/or at least one sive to FGFR1 inhibition, such as cancer, and/or at least one disease responsive to KDR inhibition, such as angiogenesis-related disorders, comprising administering to said subject in need thereof an effective amount of Form I N-(2-(dimethylamino)ethyl)-1-(3-((4-((2-methyl-1H-indol-5-yl)oxy)pyrimidin-2-yl)amino)phenyl)methanesulfonamide.

Also disclosed herein is another novel form of the compound of Formula A, designated Form II N-(2-(dimethylamino)ethyl)-1-(3-((4-((2-methyl-1H-indol-5-yl)oxy)pyrimidin-2-yl)amino)phenyl)methanesulfonamide.

Also disclosed herein are methods of preparing Form II N-(2-(dimethylamino)ethyl)-1-(3-((4-((2-methyl-1H-indol-5-yl)oxy)pyrimidin-2-yl)amino)phenyl)methanesulfonamide.

Also disclosed herein is a pharmaceutical composition, comprising at least one pharmaceutically acceptable carrier and Form II N-(2-(dimethylamino)ethyl)-1-(3-((4-((2-methyl-1H-indol-5-yl)oxy)pyrimidin-2-yl)amino)phenyl)-methanesulfonamide.

Also disclosed herein is a method of treating a subject in recognized need of treatment for at least one disease responsive to FGFR1 inhibition, such as cancer, and/or at least one disease responsive to KDR inhibition, such as angiogenesis-related disorders, comprising administering to said subject in need thereof an effective amount of Form II N-(2-(dimethylamino)ethyl)-1-(3-((4-((2-methyl-1H-indol-5-yl)oxy)pyrimidin-2-yl)amino)phenyl)methanesulfonamide.

BRIEF DESCRIPTION OF THE DRAWINGS

FIG. 1 shows a powder X-ray diffractogram of Form I N-(2-(dimethylamino)ethyl)-1-(3-((4-((2-methyl-1H-indol-5-yl)oxy)pyrimidin-2-yl)amino)phenyl)methanesulfonamide, the horizontal axis (x-axis) plots the diffraction 2 theta, and the vertical axis (y-axis) plots the intensity (counts).

FIG. 2 shows a differential scanning calorimeter (DSC) thermogram of Form I N-(2-(dimethylamino)ethyl)-1-(3-((4-((2-methyl-1H-indol-5-yl)oxy)pyrimidin-2-yl)amino)phenyl)methanesulfonamide, the horizontal axis x-axis) plots the temperature (° C.), and the vertical axis (y-axis) plots the heat flow (mW).

FIG. 3 shows a Fourier Transform-Infrared (FT-IR) spectrum of Form I N-(2-(dimethylamino)ethyl)-1-(3-((4-((2-methyl-1H-indol-5-yl)oxy)pyrimidin-2-yl)amino)phenyl)methanesulfonamide, the horizontal axis (x-axis) plots the wave number ($cm^{-1}$), and the vertical axis (y-axis) plots the transmission intensity.

FIG. 4 shows a Thermogravimetric (TG) curve of Form I N-(2-(dimethylamino)ethyl)-1-(3-((4-((2-methyl-1H-indol-5-yl)oxy)pyrimidin-2-yl)amino)phenyl)methanesulfonamide, the horizontal axis (x-axis) plots the temperature (° C.), and the vertical axis (y-axis) plots the weight percentage (%).

FIG. 5 shows a powder X-ray diffractogram of Form II N-(2-(dimethylamino)ethyl)-1-(3-((4-((2-methyl-1H-indol-5-yl)oxy)pyrimidin-2-yl)amino)phenyl)methanesulfonamide, the horizontal axis (x-axis) plots the diffraction 2 theta, and the vertical axis (y-axis) plots the intensity (counts).

FIG. 6 shows a Differential Scanning calorimeter (DSC) thermogram of Form II N-(2-(dimethylamino)ethyl)-1-(3-((4-((2-methyl-1H-indol-5-yl)oxy)pyrimidin-2-yl)amino)phenyl)methanesulfonamide, the horizontal axis x-axis) plots the temperature (° C.), and the vertical axis (y-axis) plots the heat flow (mW).

FIG. 7 shows a Fourier Transform-Infrared (FT-IR) spectrum of Form II N-(2-(dimethylamino)ethyl)-1-(3-((4-((2-methyl-1H-indol-5-yl)oxy)pyrimidin-2-yl)amino)phenyl)methanesulfonamide, the horizontal axis (x-axis) plots the wave number ($cm^{-1}$), and the vertical axis (y-axis) plots the transmission intensity.

FIG. 8 shows a Thermogravimetric (TG) curve of Form II N-(2-(dimethylamino)ethyl)-1-(3-((4-((2-methyl-1H-indol-5-yl)oxy)pyrimidin-2-yl)amino)phenyl)methanesulfonamide, the horizontal axis (x-axis) plots the temperature (° C.), and the vertical axis (y-axis) plots the weight percentage (%).

The following abbreviations and terms have the indicated meanings throughout:

The term "novel form" as used herein refers to crystalline forms Form I and Form II of the compound of Formula A and also to amorphous forms of the compound of Formula A, as well as mixtures thereof. "Crystalline form" and "polymorph," may be used interchangeably herein The term "compound of Formula A", or 'N-(2-(dimethylamino)ethyl)-1-(3-((4-((2-methyl-1H-indol-5-yl)oxy)pyrimidin-2-yl)amino)phenyl)-methanesulfonamide", is equal to a compound with the chemical structure of Formula A (also referenced as "Compound A"):

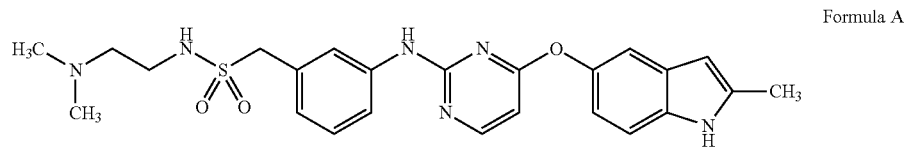

Formula A

The term "solution" means an appropriate mixture for purposes disclosed herein of one or more solutes in one or more solvents. Solution is intended to encompass homogeneous mixtures as well as heterogeneous mixtures, such as slurries or other mixtures having a suspension of insoluble (not dissolved) material.

The term "organic solvent" is broadly intended to mean any appropriate organic solvent for purposes disclosed herein.

The term "dissolution organic solvent" refers to any organic solvent that is appropriate by being capable of dissolving, in whole or in part, the substrate under suitable conditions, such as an appropriate amount and an appropriate temperature, such as room temperature or an elevated temperature.

The term "anti-dissolution organic solvent" refers to any appropriate organic solvent in which the substrate has less solubility than in the dissolution organic solvent.

"Pharmaceutically acceptable salts" include, but are not limited to salts with inorganic acids, such as hydrochlorate, hydrobromate, phosphate, diphosphate, sulfate, sulfinate, nitrate, and like salts; as well as salts with an organic acid, such as malate, maleate, mandelate, fumarate, tartrate, succinate, citrate, aspartate, glutamate, atrolactate, gluconate, propionate, lactate, camphorsulfonate, methanesulfonate, ethanesulfonate, naphthalenesulfonate, p-toluenesulfonate, 2-hydroxyethylsulfonate, hydroxybutyrate, benzoate, salicylate, stearate, and alkanoate such as acetate, HOOC—($CH_2$)n-COOH where n is 0-4, and like salts. Similarly, pharmaceutically acceptable cations include, but are not limited to, sodium, potassium, calcium, aluminum, lithium, and ammonium.

In addition, if a compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used within the realm of routine experimentation to prepare non-toxic pharmaceutically acceptable addition salts.

The term "effective amount" of the compound of Formula A, including the novel form, described herein means an amount effective, when administered to a subject in recognized need, such as a human or non-human patient, to alleviate the symptoms or stop the progression of at least one disease responsive to FGFR1 inhibition, such as cancer, and/or at least one disease responsive to KDR inhibition, such as angiogenesis-related disorders.

Provided is N-(2-(dimethylamino)ethyl)-1-(3-((4-(2-methyl-1H-indol-5-yl)oxy)pyrimidin-2-yl)amino)phenyl)methanesulfonamide of Formula A (Compound A)

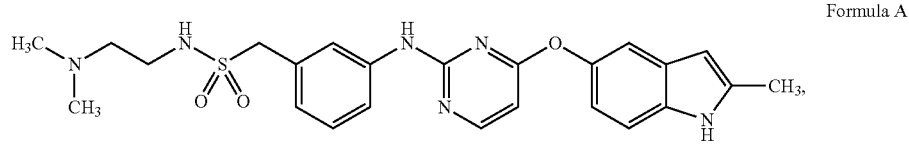

and/or pharmaceutically acceptable salts thereof.

Also provided is a pharmaceutical composition, comprising at least one pharmaceutically acceptable carrier and the compound of Formula A and/or pharmaceutically acceptable salts thereof.

The compound of Formula A can be synthesized according to the scheme described below.

Step 1: Synthesis of 5-((2-chloropyrimidin-4-yl)oxy)-2-methyl-1H-indole (Compound 3)

The title compound 3 can be prepared by the reaction of 5-hydroxyl-2-methyl-indole (compound 1) with 2,4-dichloropyrimidine (compound 2) in the presence of a base, such as but not limited to $NaHCO_3$, KOH, NaOH, $K_2CO_2$, $KHCO_3$, diisopropylethylamine (DIPEA), pyridine, triethylamine (TEA) or trimethylamine; in a solvent, such as but not limited to acetonitrile, N,N-dimethylforamide (DMF), dioxane, tetrahydrofuran (THF). The reaction may be carried out at a suitable temperature, such as a temperature ranging from 0 to 60° C.

Step 2: Synthesis of N-(2-(dimethylamino)ethyl)-1-(3-((4-((2-methyl-1H-indol-5-yl)oxy)pyrimidin-2-yl)amino)phenyl)methanesulfonamide (Compound of Formula A)

The title compound of Formula A can be synthesized as the crude product of the compound of Formula A by the reaction of Compound 3 with 1-(3-aminophenyl)-N-(2-(dimethylamino)ethyl)methane-sulfonamide (Compound 4) in the presence of an acid, such as but not limited to acetic acid, formic acid, HCl, $H_2SO_4$, toluenesulfonic acid, trifluoroacetic acid, or ethanesulfonic acid acidic, and in a solvent, such as but not limited to, N,N-dimethylformamide (DMF), acetonitrile, tetrahydrofuran, ethanol, isopropanol, or toluene. The reaction can be carried out at a suitable temperature, such as a temperature ranging from 40 to 100° C.

Scheme 1

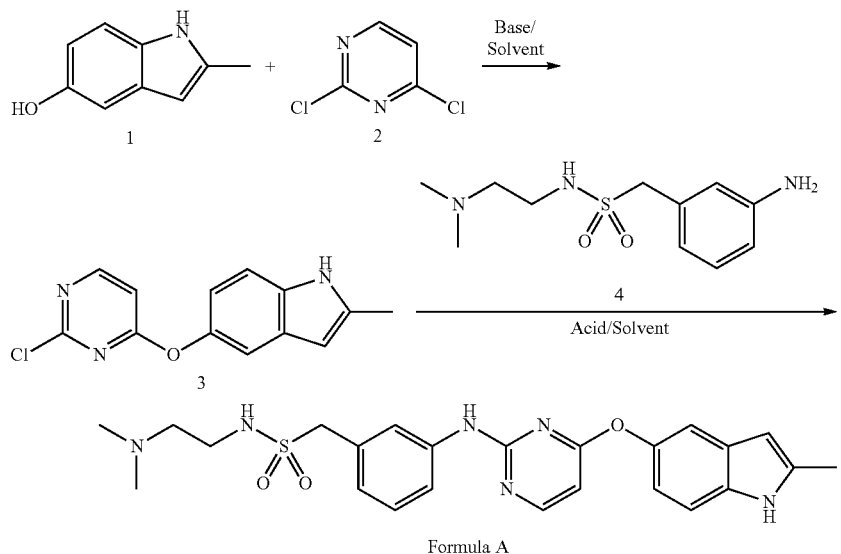

The crude product of the compound of Formula A can be further purified by chromatography on silica gel, high performance liquid chromatography, crystallization, or other suitable methods.

The crude product of the compound of Formula A can also be purified by recrystallization using solvents, such as but not limited to, N-methylpyrrolidone, dichloromethane, toluene, N,N-dimethylformamide or a mixture of N,N-dimethylformamide/toluene.

Also provided are novel forms of N-(2-(dimethylamino) ethyl)-1-(3-((4-((2-methyl-1H-indol-5-yl)oxy)pyrimidin-2-yl)amino)phenyl)methanesulfonamide.

In some embodiments, the novel forms described herein may be identified by any one or more solid state analytical methods. For example, Form I and/or Form II may be characterized according to any one or more of, e.g., X-ray diffraction, unit cell constants obtained from a single crystal, Fourier transform infrared spectroscopy, differential scanning calorimetry curve data, and a thermogravimetric curve. And if characterization by any one of those methods is consistent with the existence of Form I and/or Form II, it matters not that one of the other methods is inconsistent with that existence.

In some embodiments, the novel forms described herein may be characterized according to X-ray powder diffraction. However, it is known in the art that the intensity and/or measured peaks in the X-ray powder diffractogram of different batches of a novel form may vary, because of, for example, different experimental conditions and/or preferred orientations. And according to the instrument precision, the measurement error of 2θ value is at ±0.2 2θ. But notwithstanding experimental and machine errors, and principles such as preferred orientation, one skilled in the art can find sufficient information in the XRPD data provided herein to identify Form I and Form II without having to rely on all the XRPD data provided.

Form I N-(2-(dimethylamino)ethyl)-1-(3-((4-((2-methyl-1H-indol-5-yl)oxy)pyrimidin-2-yl)amino) phenyl)methanesulfonamide Provided is Form I N-(2-(dimethylamino)ethyl)-1-(3-((4-((2-methyl-1H-indol-5-yl)oxy)pyrimidin-2-yl)amino)phenyl)methanesulfonamide.

In some embodiments, the X-ray powder diffractogram of the Form I as described herein may have peaks (2θ) chosen from those having about the following values: 7.0, 8.0, and 8.6, each of the diffraction angles being ±0.2 degrees (2θ). In some embodiments, the X-ray powder diffractogram of the Form I as described herein may have peaks (2θ) chosen from those having about the following values: 7.0, 8.0, 8.6, 11.0, 11.8, each of the diffraction angles being ±0.2 degrees (2θ). In some embodiments, the Form I as described herein may have a X-ray powder diffractogram substantially similar to that shown in FIG. 1.

In some embodiments, Form I N-(2-(dimethylamino)ethyl)-1-(3-((4-((2-methyl-1H-indol-5-yl)oxy)pyrimidin-2-yl)amino)phenyl)methanesulfonamide may be characterized according to Fourier Transform-Infrared (FT-IR) spectrum. For example, also provided is an embodiment of Form I N-(2-(dimethylamino)ethyl)-1-(3-((4-((2-methyl-1H-indol-5-yl)oxy)pyrimidin-2-yl)amino)phenyl)-methanesulfonamide having a FT-IR spectrum showing peaks at about 2781.4, 1218.2, 1163.1, 1124.5, 1114.8, 1085.7, 984.9, 705.0, 500.7, and 434.8 $cm^{-1}$. In some embodiments, the Form I as described herein may have an FT-IR spectrum substantially similar to that shown in FIG. 3.

In some embodiments, Form I N-(2-(dimethylamino)ethyl)-1-(3-((4-((2-methyl-1H-indol-5-yl)oxy)pyrimidin-2-yl)amino)phenyl)methanesulfonamide may be characterized according to a DSC thermogram. For example, provided is an embodiment of the Form I as described herein having a DSC thermogram substantially similar to that shown in FIG. 2. For example, also provided is an embodiment of the Form I as described herein having a DSC with endothermic peaks at about 167-169° C.

In some embodiments, Form I N-(2-(dimethylamino)ethyl)-1-(3-((4-((2-methyl-1H-indol-5-yl)oxy)pyrimidin-2-yl)amino)phenyl)methanesulfonamide may be characterized by thermogravimetric analysis (TGA). For example, provided is an embodiment of the Form I as described herein having a TGA indicating the Form I as described herein as anhydrous or neat form. See FIG. 4.

In some embodiments, Form I is substantially free of Form II and of the amorphous form of the compound of Formula A. For example, Form I is at least 99%, at least 95%, at least 90%, or at least 80%, by weight, free of Form II and of the amorphous form of the compound of Formula A. Further for example, Form I is at least 70%, or at least 60%, by weight, free of Form II and of the amorphous form of the compound of Formula A. Even further for example, Form I is at least more than 50% by weight free of Form II and of the amorphous form of the compound of Formula A.

Methods of Preparing Form I N-(2-(dimethylamino)ethyl)-1-(3-((4-((2-methyl-1H-indol-5-yl)oxy)pyrimidin-2-yl)amino)phenyl)methanesulfonamide Method A Also provided is a method of preparing Form I N-(2-(dimethylamino)ethyl)-1-(3-((4-((2-methyl-1H-indol-5-yl)oxy) pyrimidin-2-yl)amino)phenyl)methanesulfonamide, comprising:

(1) mixing N-(2-(dimethylamino)ethyl)-1-(3-((4-((2-methyl-1H-indol-5-yl)oxy)pyrimidin-2-yl)amino)phenyl) methanesulfonamide of Formula A with at least one dissolution organic solvent, then heating the mixture to reflux to obtain a solution;

(2) cooling the solution to ambient temperature, such as slowly cooling; and (3) isolating Form I N-(2-(dimethylamino)ethyl)-1-(3-((4-((2-methyl-1H-indol-5-yl)oxy)pyrimidin-2-yl)amino)phenyl)methanesulfonamide.

In some embodiments, the at least one appropriate dissolution organic solvent is chosen from protic solvents and aprotic solvents. In some embodiments, the protic solvents are alcohols, such as methanol, ethanol, isopropanol, n-butanol, and alcohols comprising less than 6 carbon atoms, further such as methanol, ethanol, and isopropanol. In some embodiments, the aprotic solvents are chosen from acetone, acetonitrile, N,N-dimethylformamide, toluene, dichloromethane, and ethyl acetate.

In some embodiments, the solution is cooled to ambient temperature, such as slowly cooled while stirring, such as stirring at a moderate rate, further such as at a rate ranging from 50 to 200 rpm.

In some embodiments, the amount of the at least one dissolution solvent is 10 to 60 volumes (ml) to 1 unit weight (g) of the compound of Formula A used in step (1).

Method B

Also provided is an alternative method of preparing Form I N-(2-(dimethylamino)ethyl)-1-(3-((4-((2-methyl-1H-indol-5-yl)oxy)pyrimidin-2-yl)amino)phenyl), comprising:

(1) mixing N-(2-(dimethylamino)ethyl)-1-(3-((4-((2-methyl-1H-indol-5-yl)oxy)pyrimidin-2-yl)amino)phenyl)methanesulfonamide with at least one dissolution organic solvent, then heating the mixture to reflux to obtain a first solution;

(2) adding at least one anti-dissolution organic solvent to the first solution at refluxing temperature to obtain a second solution;

(3) leaving the second solution to cool, such as cool slowly, on its own to ambient temperature; and (4) isolating Form I N-(2-(dimethylamino)ethyl)-1-(3-((4-((2-methyl-1H-indol-5-yl)oxy)pyrimidin-2-yl)amino)phenyl)methanesulfonamide.

In some embodiments, the at least one dissolution solvent is as described above. In some embodiments, the at least one dissolution solvent is chosen from methanol, ethanol, acetone, acetonitrile, and N,N-dimethylformamide.

In some embodiments, the appropriate anti-dissolution solvent, depending on the conditions, is chosen from water, heptanes, hexanes, and other saturated hydrocarbon solvents with less than nine carbon atoms; ethyl acetate, and other organic acid esters with less than eight carbon atoms; t-butyl methyl ether, and other ethers with less than six carbon atoms; and toluene. In some embodiments, the at least one anti-dissolution solvent is chosen from water, heptanes, hexanes, and ethyl acetate.

In some embodiments, the volume ratio of the at least one dissolution solvent to the at least one anti-dissolution solvent ranges from 1:3 to 5:1.

In some embodiments, the amount of the at least one dissolution solvent used in this alternative method is also 10 to 60 volumes (ml) to 1 unit weight (g) of the compound of Formula A used in step (1).

Form II N-(2-(dimethylamino)ethyl)-1-(3-((4-((2-methyl-1H-indol-5-yl)oxy)pyrimidin-2-yl)amino)phenyl)methanesulfonamide Also provided is Form II N-(2-(dimethylamino)ethyl)-1-(3-((4-((2-methyl-1H-indol-5-yl)oxy)pyrimidin-2-yl)amino)phenyl)methane-sulfonamide.

In some embodiments, Form II N-(2-(dimethylamino)ethyl)-1-(3-((4-((2-methyl-1H-indol-5-yl)oxy)pyrimidin-2-yl)amino)phenyl)methanesulfonamide may be characterized according to X-ray powder diffraction. In some embodiments, the X-ray powder diffractogram of the Form II as described herein may have peaks (2θ) chosen from those having about the following values: 6.8, 9.8, 10.5, and 10.7, each of the diffraction angles being ±0.2 degrees (2θ). In some embodiments, the X-ray powder diffractogram of the Form II as described herein may have peaks (2θ) chosen from those having about the following values: 6.8, 9.8, 10.5, 10.7, 13.6, 15.0, each of the diffraction angles being ±0.2 degrees (2θ). In some embodiments, the Form II as described herein may have a X-ray powder diffractogram substantially similar to that shown in FIG. 5. But notwithstanding experimental and machine errors, and principles such as preferred orientation, one skilled in the art can find sufficient information in the XRPD data provided herein to identify a Form II without having to rely on all the XRPD data provided.

In some embodiments, Form II N-(2-(dimethylamino)ethyl)-1-(3-((4-((2-methyl-1H-indol-5-yl)oxy)pyrimidin-2-yl)amino)phenyl)methanesulfonamide may be characterized according to Fourier Transform-Infrared (FT-IR) spectrum. For example, also provided is an embodiment of Form II N-(2-(dimethylamino) ethyl)-1-(3-((4-((2-methyl-1H-indol-5-yl)oxy)pyrimidin-2-yl)amino)phenyl)methanesulfonamide having a FT-IR spectrum showing peaks at about 2770.3, 1216.3, 1166.3, 1115.8, 1089.8, 986.5, 872.5, 695.5, 520.5, 456.0 cm$^{-1}$. In some embodiments, the Form II as described herein may have a FT-IR spectrum substantially similar to that shown in FIG. 7.

In some embodiments, Form II N-(2-(dimethylamino)ethyl)-1-(3-((4-((2-methyl-1H-indol-5-yl)oxy)pyrimidin-2-yl)amino)phenyl)methanesulfonamide may be characterized according to a DSC thermogram. For example, provided is an embodiment of the Form II as described herein having a DSC thermogram substantially similar to that shown in FIG. 6. For example, also provided is an embodiment of the Form II as described herein having a DSC with endothermic peaks at about 160-162° C. See FIG. 6.

In some embodiments, Form II N-(2-(dimethylamino)ethyl)-1-(3-((4-((2-methyl-1H-indol-5-yl)oxy)pyrimidin-2-yl)amino)phenyl)methanesulfonamide may be characterized by thermogravimetric analysis (TGA). For example, provided is an embodiment of the Form II as described herein having a TGA indicating the Form II as described herein as anhydrous or neat form. See FIG. 8.

In some embodiments, Form II is substantially free of Form I and of the amorphous form of the compound of Formula A. For example, Form II is at least 99%, at least 95%, at least 90%, or at least 80%, by weight, free of Form I and of the amorphous form of the compound of Formula A. Further for example, Form II is at least 70%, or at least 60%, by weight, free of Form I and of the amorphous form of the compound of Formula A. Even further for example, Form II is at least more than 50% by weight free of Form I and of the amorphous form of the compound of Formula A.

Method of Preparing Form II N-(2-(dimethylamino)ethyl)-1-(3-((4-((2-methyl-1H-indol-5-yl)oxy)pyrimidin-2-yl)amino)phenyl)-methanesulfonamide Method C Also provided is a method of preparing Form II N-(2-(dimethylamino) ethyl)-1-(3-((4-((2-methyl-1H-indol-5-yl)oxy)pyrimidin-2-yl)amino)phenyl)methanesulfonamide, comprising (1) mixing N-(2-(dimethylamino)ethyl)-1-(3-((4-((2-methyl-1H-indol-5-yl)oxy)pyrimidin-2-yl)amino)phenyl)methanesulfonamide with at least one dissolution solvent, and heating the mixture to reflux to obtain a first solution;

(2) adding at least one anti-dissolution solvent to the first solution at reflux temperature to obtain a second solution;

(3) cooling the second solution, for example, to 0-5° C., for example at a cooling rate of 1-40° C./minute; and (4) isolating Form II N-(2-(dimethylamino)ethyl)-1-(3-((4-((2-methyl-1H-indol-5-yl)oxy)pyrimidin-2-yl)amino)phenyl)methanesulfonamide.

In some embodiments, the solution is cooled to 0-5° C. at a cooling rate of 1-40° C./minute while stirring.

In some embodiments, the at least one appropriate dissolution organic solvent is chosen from protic solvents and aprotic solvents. In some embodiments, the protic solvents are alcohols, such as methanol, ethanol, isopropanol, n-butanol, and alcohols comprising less than 6 carbon atoms, further such as methanol, ethanol, and isopropanol. In some embodiments, the aprotic solvents are chosen from acetone, acetonitrile, N,N-dimethylformamide, toluene, dichloromethane, and ethyl acetate.

In some embodiments, the appropriate alcohols are chosen from methanol and ethanol. In some embodiments, the aprotic solvents are chosen from acetone, acetonitrile, ethyl acetate, and N,N-dimethylformamide.

In some embodiments, the ratio of the weight of the compound of Formula A to the volume of the at least one dissolution solvent ranges from 0.03:1 to 0.08:1 (g/ml).

Method D

Also provided is an alternative method of preparing Form II N-(2-(dimethylamino)ethyl)-1-(3-((4-((2-methyl-1H-indol-5-yl)oxy)pyrimidin-2-yl)amino)phenyl)methanesulfonamide, comprising:

(1) mixing N-(2-(dimethylamino)ethyl)-1-(3-((4-((2-methyl-1H-indol-5-yl)oxy)pyrimidin-2-yl)amino)phenyl) methanesulfonamide with at least one dissolution solvent, and heating the mixture to reflux to obtain a solution;

(2) cooling the solution; then seeding the cooled solution with the Form II as described herein;

(3) cooling the seeded solution to ambient temperature; and (4) isolating Form II N-(2-(dimethylamino)ethyl)-1-(3-((4-((2-methyl-1H-indol-5-yl)oxy)pyrimidin-2-yl)amino) phenyl)methanesulfonamide.

In some embodiments, the solution in step (2) is slowly cooled to 45-55° C. before the seeding.

In some embodiments, the Form II seed is added to the solution while stirring.

In some embodiments, the seeded solution is cooled to ambient temperature by leaving the seeded solution at ambient temperature.

In some embodiments, the at least one appropriate dissolution organic solvent is chosen from protic solvents and aprotic solvents. In some embodiments, the protic solvents are alcohols, such as methanol, ethanol, isopropanol, n-butanol, and alcohols comprising less than 6 carbon atoms, further such as methanol, ethanol, and isopropanol. In some embodiments, the aprotic solvents are chosen from acetone, acetonitrile, N,N-dimethylformamide, toluene, dichloromethane, and ethyl acetate.

In some embodiments, the appropriate alcohols are chosen from methanol and ethanol. In some embodiments, the aprotic solvents are chosen from acetone, acetonitrile, ethyl acetate, and N,N-dimethylformamide In some embodiments, the Form II seed is added to the solution with stirring.

In some embodiments, the ratio of the weight of the compound of Formula A to the volume of the at least one dissolution solvent (g/ml) ranges from 0.03:1 to 0.08:1.

In some embodiments, the amount of the Form II seed ranges from 0.01 to 0.5% by weight relative to the weight of N-(2-(dimethylamino)ethyl)-1-(3-((4-((2-methyl-1H-indol-5-yl)oxy)pyrimidin-2-yl)amino)phenyl)methanesulfonamide used in step (1). In some embodiments, the amount of the Form II seed is 0.5% by weight relative to the weight of N-(2-(dimethylamino)ethyl)-1-(3-((4-((2-methyl-1H-indol-5-yl)oxy)pyrimidin-2-yl)amino)phenyl)methanesulfonamide used in step (1).

All of the methods as described herein of preparing Form I or Form II N-(2-(dimethylamino)ethyl)-1-(3-((4-((2-methyl-1H-indol-5-yl)oxy)pyrimidin-2-yl)amino)phenyl)methanesulfonamide may optionally further comprise one more step between step (1) and step (2), wherein the solution obtained in step (1) is hot filtered to remove insoluble particulates. To avoid precipitation during any hot filtration, the filtration funnel used can be warmed during or before the filtration. Precipitates formed during hot filtration can be re-dissolved by heating the filtrates before the next operation.

Pharmaceutical Composition and Methods of Treatment

In some embodiments, at least one active pharmaceutical ingredient chosen from the compound of Formula A (Compound A) and/or pharmaceutically acceptable salts thereof, and Forms I and II of the compound of Formula A may be useful for the treatment of at least one disease responsive to FGFR1 inhibition, such as cancer, and/or at least one disease responsive to KDR inhibition, such as angiogenesis-related disorders. In some embodiments, the angiogenesis related disorders are chosen from age-related macular degeneration and cancers. Cancers as described herein include but are not limited to liver cancer, lung cancer, head and neck cancer, breast cancer, bladder cancer, colorectal cancer, gastric cancer, pancreatic cancer, ovarian cancer, prostate cancer, kidney cancer, and sarcoma.

In some embodiments, the method of treating a subject having at least one cancer and/or at least one angiogenesis-related disease and in recognized need of treatment therefor comprises administering to said subject in recognized need of treatment an effective amount of at least one active pharmaceutical ingredient chosen from the compound of Formula A and/or pharmaceutically acceptable salts thereof, and Forms I and II of the compound of Formula A to treat said at least one disease responsive to FGFR1 inhibition, such as cancer, and/or at least one disease responsive to KDR inhibition, such as angiogenesis-related disorders.

In some embodiments, the method of treating a subject having at least one disease responsive to FGFR1 inhibition, such as cancer, and/or at least one disease responsive to KDR inhibition, such as angiogenesis-related disorders and in recognized need of treatment therefor comprises administering to said subject in recognized need of treatment an effective amount of Form I N-(2-(dimethylamino)ethyl)-1-(3-((4-((2-methyl-1H-indol-5-yl)oxy)pyrimidin-2-yl)amino)phenyl) methanesulfonamide, to treat said at least one disease responsive to FGFR1 inhibition, such as cancer, and/or at least one disease responsive to KDR inhibition, such as angiogenesis-related disorders.

In some embodiments, the method of treating a subject having at least one disease responsive to FGFR1 inhibition, such as cancer, and/or at least one disease responsive to KDR inhibition, such as angiogenesis-related disorders and in recognized need of treatment therefor comprises administering to said subject in recognized need of treatment an effective amount of Form II N-(2-(dimethylamino)ethyl)-1-(3-((4-((2-methyl-1H-indol-5-yl)oxy)pyrimidin-2-yl)amino)phenyl) methanesulfonamide, to treat said at least one disease responsive to FGFR1 inhibition, such as cancer, and/or at least one disease responsive to KDR inhibition, such as angiogenesis-related disorders.

In some embodiments, the method of treating a subject having at least one disease responsive to FGFR1 inhibition, such as cancer, and/or at least one disease responsive to KDR inhibition, such as angiogenesis-related disorders and in recognized need of treatment therefor comprises administering to said subject in recognized need of treatment an effective amount of a pharmaceutical composition comprising: at least one pharmaceutically acceptable carrier and the compound of Formula A and/or pharmaceutically acceptable salts thereof, to provide said treatment.

In some embodiments, the method of treating a subject having at least one disease responsive to FGFR1 inhibition, such as cancer, and/or at least one disease responsive to KDR inhibition, such as angiogenesis-related disorders and in recognized need of treatment therefor comprises administering to said subject in recognized need of treatment an effective amount of a pharmaceutical composition comprising: at least one pharmaceutically acceptable carrier and Form I N-(2-(dimethylamino)ethyl)-1-(3-((4-((2-methyl-1H-indol-5-yl) oxy)pyrimidin-2-yl)amino)phenyl), to provide said treatment.

In some embodiments, the method of treating a subject having at least one disease responsive to FGFR1 inhibition, such as cancer, and/or at least one disease responsive to KDR inhibition, such as angiogenesis-related disorders and in recognized need of treatment therefor comprises administering to said subject in recognized need of treatment an effective amount of a pharmaceutical composition comprising: at least one pharmaceutically acceptable carrier and Form II N-(2-(dimethylamino)ethyl)-1-(3-((4-((2-methyl-1H-indol-5-yl)oxy)pyrimidin-2-yl)amino)phenyl)methanesulfonamide, to provide said treatment.

The amount of the at least one active pharmaceutical ingredient chosen from the compound of Formula A and/or pharmaceutically acceptable salts thereof and Forms I and II of the compound of Formula A effective for achieving the desired biological effect may depend on a number of factors, for example, the intended use, the mode of administration, and the clinical condition of the patient. The daily dose may, for example, range from 0.1 mg to 3 g/day (such as from 0.5 mg to 2 g/day, further such as from 100 mg to 1 g/day). Single-dose formulations which can be administered orally include, for example, tablets or capsules.

For the therapy of the above-mentioned conditions, the at least one active pharmaceutical ingredient chosen from the compound of Formula A and/or pharmaceutically acceptable salts thereof and Forms I and II of the compound of Formula A may be used as the compound itself, but typically each of them would be used in the form of a pharmaceutical composition with one or more acceptable carriers/excipients. Representative carriers/excipients should be compatible with the other ingredients of the composition and not harmful for the patient's health. The carrier/excipient may be a solid or a liquid or both and may be formulated with the compound of Formula A, such as Form I and/or Form II described herein, as a single dose, for example as a tablet, which may be prepared from 0.05% to 95% by weight of the compound of Formula A described herein. The pharmaceutical compositions described herein can be produced by known pharmaceutical methods, such as those involving mixing the ingredients with pharmacologically acceptable carriers and/or excipients and/or diluents.

In some embodiments, representative carriers/excipients would include but are not limited to: microcrystalline cellulose, lactose, sodium citrate, calcium carbonate, dicalcium phosphate, glycine, disintegrants such as starch, sodium cross-linked carboxymethyl cellulose, composite silicates, and polyethylene glycol with high molecular weight, granulation binders (such as polyvinylpyrrolidone, sucrose, gelatin, and Gum Arabic), and lubricants (such as magnesium stearate, glycerin, and talc).

In some embodiments, the at least one active pharmaceutical ingredient chosen from the compound of Formula A and/or pharmaceutically acceptable salts thereof and Forms I and II of the compound of Formula A may be combined with at least one component, such as carrier and/or excipient and/or diluent, chosen from sweeteners, delicate flavor agents, coloring matters, dyes, and emulsifiers.

In some embodiments, the Form I or Form II described herein may not be converted upon formulation with the one or more pharmaceutically acceptable diluents. In other embodiments, the Form I or Form II described herein may be converted, in whole or in part, to one or more other forms, including a non-solid form, upon formulation with the one or more pharmaceutically acceptable carriers/diluents/excipients. Exemplary carriers/diluents/excipients would include but are not limited to, water, ethanol, propylene glycol, glycerine, and mixtures thereof. In some embodiments, the Form I or Form II described herein can be dissolved when formulated into a pharmaceutical composition. Accordingly, in such "dissolved" cases, the Form I or Form II no longer exists in their respective crystalline forms in the pharmaceutical composition.

In some embodiments, the at least one active pharmaceutical ingredient chosen from the compound of Formula A and/or pharmaceutically acceptable salts thereof and Forms I and II of the compound of Formula A may be formulated to a suitable form.

Pharmaceutical compositions described herein can be those suitable for oral and peroral (for example sublingual) administration, although the suitable mode of administration may depend in each individual case on the nature and severity of the condition to be treated and on the nature of the at least one active pharmaceutical ingredient chosen from the compound of Formula A and/or pharmaceutically acceptable salts thereof and Forms I and II of the compound of Formula A used in each case to prepare the pharmaceutical composition. Coated formulations and coated slow-release formulations also are provided. Acid- and gastric juice-resistant formulations are possible. Suitable coatings resistant to gastric juice comprise cellulose acetate phthalate, polyvinyl acetate phthalate, hydroxypropylmethylcellulose phthalate, anionic polymers of methacrylic acid, and methyl methacrylate.

Suitable pharmaceutical compositions for oral administration prepared from the at least one active pharmaceutical ingredient chosen from the compound of Formula A and/or pharmaceutically acceptable salts thereof and Forms I and II of the compound of Formula A may be in the form of separate units such as, for example, capsules, cachets, and tablets, including suckable tablets, each of which may be prepared with a defined amount of the at least one active pharmaceutical ingredient described herein; as well as in the forms chosen from powders, granules, solutions, suspensions in an aqueous or nonaqueous liquid, and oil-in-water and water-in-oil emulsions. Those compositions may, as already mentioned, be prepared by any suitable pharmaceutical formulation method, such as those including a step wherein the at least one active pharmaceutical ingredient chosen from the compound of Formula A and/or pharmaceutically acceptable salts thereof and Forms I and II of the compound of Formula A and a carrier (which may consist of one or more additional ingredients, including diluents and excipients) are brought into contact. The compositions can generally be produced by uniform and homogeneous mixing of the at least one active pharmaceutical ingredient chosen from the compound of Formula A and/or pharmaceutically acceptable salts thereof and Forms I and II of the compound of Formula A with a liquid and/or finely divided solid carrier, after which the product can be shaped. Thus, for example, a tablet can be produced by compressing or molding a powder or granules of the at least one active pharmaceutical ingredient chosen from the compound of Formula A and/or pharmaceutically acceptable salts thereof and Forms I and II of the compound of Formula A, where appropriate with one or more additional ingredients. Compressed tablets can be produced by tableting the at least one active pharmaceutical ingredient chosen from the compound of Formula A and/or pharmaceutically acceptable salts thereof and Forms I and II of the compound of Formula A in free-flowing form such as, for example, a powder or granules, where appropriate mixed with a binder, glidant, inert diluent and/or one (or more) surface-active/dispersing agent(s) in a suitable machine. Molded tablets can be produced by molding the at least one active pharmaceutical ingredient chosen from the compound of Formula A and/or pharmaceutically acceptable salts thereof and Forms I and II of the compound of Formula A in powder form and then moistening with an inert liquid diluent, in a suitable machine. Compositions can also be prepared by wet granulation. Thus, for example, a composition can be prepared by wet granulation by mixing the at least one active pharmaceutical ingredient chosen from the compound of Formula A and/or pharmaceutically acceptable salts thereof and Forms I and II of the compound of Formula A with one or more optional additional ingredients, a suitable solvent, and a binder to prepare a wet granulate, drying the wet granulate, and milling the dried granulate. The method may further comprise adding at least one lubricant to the dried milled granulate and compressing the dried milled granulate to form tablets. The optional additional ingredients may include, for example, at least one diluent and/or at least one disintegration agent. The suitable solvent can be water. In some embodiments, the diluent is chosen from calcium carbonate, calcium phosphate (dibasic and/or tribasic), calcium sulfate, powdered cellulose, dextrates, dextrin, fructose, kaolin, lactitol, anhydrous lactose, lactose monohydrate, maltose, mannitol, microcrystalline cellulose, sorbitol, sucrose, and starch. In some embodiments, the diluent can be present in an amount from about 35% to about 90% by weight of the tablet. In some embodiments, the binder can be chosen from acacia, alginic acid, carbomer, sodium carboxymethylcellulose, dextrin, ethylcellulose, gelatin, glucose, guar gum, hydroxypropyl cellulose, maltose, methylcellulose, polyethylene oxide, and povidone. In some exemplary embodiments, the binder is present in an amount of about 0.5% to about 5% by weight of the tablet. In other exemplary embodiments, the above-mentioned preparations contain about 0.05-5 g of the at least one active pharmaceutical ingredient chosen from the compound of Formula A and/or pharmaceutically acceptable salts thereof and Forms I and II of the compound of Formula A per milliliter or per gram of the preparations.

The compositions disclosed herein can be administered topically or systemically.

Pharmaceutical compositions which are suitable for peroral (sublingual) administration can comprise suckable tablets which can be prepared from the at least one active pharmaceutical ingredient chosen from the compound of Formula A and/or pharmaceutically acceptable salts thereof and Forms I and II of the compound of Formula A, with a flavoring agent, normally chosen from sucrose, gum arabic, tragacanth, and pastilles.

Pharmaceutical compositions described herein can also be those suitable for parenterally administration, by inhalation spray, or via an implanted reservoir. Solid carriers, for example, starch, lactose, Microcrystalline Cellulose, aluminum silicate, liquid carriers, for example, injectable water, polyvinyl alcohol, non-ionized surfactant agents, and corn oil, and any ingredients suitable for intend use. Other excipients commonly used in pharmaceutical formulation include coloring agents, preservatives, taste correctives agents and antioxidants such as vitamin E, vitamin A, BHT and BHA.

The compound of Formula A, such as the Form I or Form II described herein, can also be administered intraperitoneally. And the solution and suspension of those compounds can be prepared by dissolving or suspended the compound in water containing suitable surfactants. Dispersed suspensions can be prepared by using glycerol, polyethylene glycol (PEG) or their mixture with suitable oils. Preservatives agents can be added to those formulations to prevent growth of microorganisms during use.

Injectable formulation includes solution or suspension in sterilized water, and sterilized powder. In all cases, those formulations must be sterilized and easily removed from the syringe, and stable under the manufacture and storage conditions, and as free as possible from pollution and the effects of microorganisms. Carriers can be solvents or dispersing agents, and include water, alcohol, and some suitable oils.

The at least one active pharmaceutical ingredient chosen from the compound of Formula A and/or pharmaceutically acceptable salts thereof and Forms I and II of the compound of Formula A can also be administered in combination with one or more other active ingredients. When administered as a combination, the active ingredients can be formulated as separate compositions that are administered at the same time or sequentially at different times, or the active ingredients can be administered in a single dosage form, i.e., single composition, provided that the active ingredients are not, in that single dosage form, incompatible with other active ingredients or the formulation, or otherwise undesirably combined in a single composition.

In some embodiments, the at least one active pharmaceutical ingredient chosen from the compound of Formula A and/or pharmaceutically acceptable salts thereof and Forms I and II of the compound of Formula A can be administered with one or more other agents known for the treatment of at least one disease responsive to FGFR1 inhibition, such as cancer, and/or at least one disease responsive to KDR inhibition, such as angiogenesis-related disorders.

The phrase "co-therapy" (or "combination-therapy") or "in combination with", as used herein, defines the use of the at least one active pharmaceutical ingredient chosen from the compound of Formula A and/or pharmaceutically acceptable salts thereof and Forms I and II of the compound of Formula A as described herein and one or more other active ingredients, such as, for example, anti-neoplastic agents. As used herein, the term "anti-neoplastic agent" refers to any agent that is administered to a subject with cancer for purposes of treating the cancer. Non-limiting examples anti-neoplastic agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed, or activated in cancers, the inhibition of which downregulates cell replication.

In co-therapy, administration of each active ingredient can occur in a sequential manner in a regimen to provide beneficial effects of the drug combination; and/or co-administration of the aforementioned components can occur in a substantially simultaneous manner (e.g., as in a single dosage form, such as a capsule, having a fixed ratio of the active ingredients or in multiple, separate capsules for each active ingredient, etc.).

Thus, methods described herein are not limited in the sequence of administration; the at least one active pharmaceutical ingredient chosen from the compound of Formula A and/or pharmaceutically acceptable salts thereof and Forms I and II of the compound of Formula A described herein may be administered either prior to, at the same time with or after administration of the one or more other active ingredients.

The following non-limiting examples are provided.

EXPERIMENTS

All reagents, except intermediates, used in this disclosure are commercially available. All compound names except the reagents were generated by ChemBioDraw Ultra 12.0.

Unless otherwise indicated, powder X-ray diffractograms were obtained using Bruker D8 ADVANCE X-ray diffractometer, with radiation generated from a CuKa source at 40 mA and 40 kV, and the instrument can be operated over the 2θ range of 3-45° with scan step of 0.02° and scanning speed at 4°/min.

DSC thermal analyses were performed on PerkinElmer DSC 7, in which nitrogen was used as the purge gas at a flow rate of 50 mL min$^{-1}$. The samples were measured in crimped aluminum pans. The instruments were calibrated for temperature using indium. Sample tests of DSC experiments were carried out in the conventional mode at a heating rate of 5-10° C. min$^{-1}$ with the temperature ranging from 25 to 200° C.

The IR spectra were recorded using the MagnaTI-IR750 (NICOLET) spectrometer, each sample was pressed to KBr discs.

Thermogravimetric (TG) curves, which can be used to determine the weight changes of the materials as a function of temperature, were obtained by using Perkin-Elmer Thermal TGA7, with $N_2$ as a purging gas at a flow rate of 50 mL min$^{-1}$, the heating rate is 10° C./min.

Example 1

Synthesis of N-(2-(dimethylamino)ethyl)-1-(3-((4-((2-methyl-1H-indol-5-yl)oxy)pyrimidin-2-yl)amino)phenyl)methanesulfonamide Step 1: Synthesis of 5-((2-chloropyrimidin-4-yl)oxy)-2-methyl-1H-indole (Compound 3)

To a 50 L three-neck round bottom flask, equipped with a mechanical stirrer, addition funnel and thermometer, were added 2-methyl-1H-indol-5-ol (compound 1, 3 Kg), anhydrous acetonitrile (9 L) and potassium carbonate (4.2 Kg). The reaction mixture was cooled to 0-5° C. with stirring under $N_2$. A solution of 2,4-dichloropyrimidine (Compound 2, 3.05 Kg, in 9 L of acetonitrile) was added to the reaction mixture dropwise while keeping the inner temperature of the reaction in the range from 0 to 5° C. After addition was complete, the reaction mixture was allowed to warm to a temperature ranging from 5 to 10° C. over a period of 4-8 hours. When reaction was completed, the reaction mixture was poured into 54 L of distilled water in a 100 L reactor with stirring, and stirred for another hour at room temperature. The precipitates were collected by filtration and the filter cake was washed with pure water to afford Compound 3 (5.7 Kg).

Step 2: Synthesis of N-(2-(dimethylamino)ethyl)-1-(3-((4-((2-methyl-1H-indol-5-yl)oxy)pyrimidin-2-yl)amino)phenyl)methanesulfonamide (Compound of Formula A)

To a 10 L three-necked round bottom flask, equipped with a mechanical stirrer and a thermometer, were added Compound 3 (1.05 Kg), 1-(3-aminophenyl)-N-(2-(dimethylamino)ethyl)methanesulfonamide (Compound 4, 1.06 Kg), p-toluenesulfonic acid (0.86 Kg), and N,N-dimethylformamide (5.25 L). The reaction mixture was carefully warmed to a temperature ranging from 55 to 65° C., and stirred at this temperature for 16-20 hours. After the completion of the reaction, the reaction mixture was cooled to room temperature, and was transferred portion-wise to a solution of 5% aqueous potassium carbonate. When the addition was complete, the obtained slurry was stirred for another 1-2 hours. Crude product was collected by filtration, and the wet filter cake was transferred to a 200 L reactor.

To the reactor, toluene (104 Kg) was added, and the suspension was heated to reflux to remove water by a Dean-Stark trap. After the removal of water, the solution was concentrated to a final volume of 30-40 L under reduced pressure, cooled to 15-20° C. The product was collected and dried to afford the title product (Compound of Formula A, 1.07 Kg). This material can then be used to produce novel forms of the compound of Formula A, such as Form I and/or Form II.

Example 2

In Vitro Studies of KDR Kinase Inhibition Activity

Compounds tested:

N-(2-(dimethylamino)ethyl)-1-(3-((4-((2-methyl-1H-indol-5-yl)oxy)pyrimidin-2-yl)amino)phenyl)methanesulfonamide (Compound of Formula A)

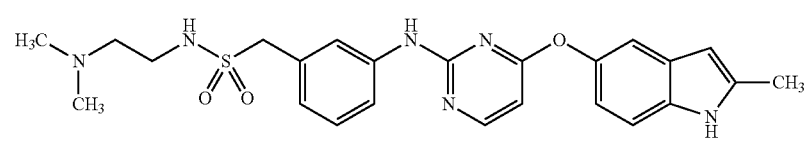

Formula A

N-methyl-1-(3-((4-((2-methyl-1H-indol-5-yl)oxy)pyrimidin-2-yl)amino)phenyl)methanesulfonamide (Compound of Formula B)

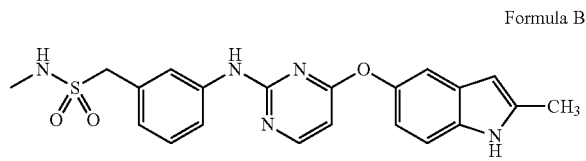

Formula B $N^4$-(4-fluoro-2-methyl-1H-indol-5-yl)-$N^2$-(3-(2-morpholinoethoxy)phenyl)pyrimidine-2,4-diamine (Compound of Formula C)

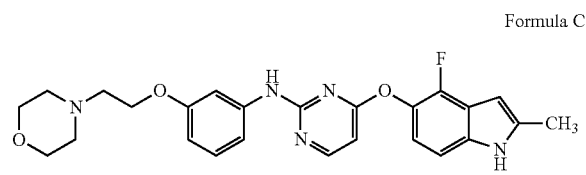 [SMILES: Cc1cc2c(F)c(Oc3ccnc(Nc4cccc(OCCN5CCOCC5)c4)n3)ccc2[nH]1]

Formula C

The KDR kinase inhibition activity of the above three compounds is tested using the Z-Lyte assay kit.

Materials and Method:

Z'-LYTET™ Tyr1 peptide (Invitrogen, Cat. PV3190) is used to test the KDR kinase inhibitory activity of the above three compounds. The testing system contains 300 ng/mL of recombinant human KDR catalytic domain, 10 µM of ATP, 1 µM of substrate peptide, and a test compound at a series of different concentrations in 384-well plate (Thermo Labsystems, Cat. 7805); total volume is 10 µL. The enzymatic inhibition proceeds at room temperature (25° C.) for 1 hour on the shaker, followed by addition of 5 µL of enhancer and incubation for an additional 1 hour at room temperature on the shaker. 5 µL of stop solution is added to stop the reaction. The KDR kinase inhibition activity of a test compound is calculated based on the method recommended by the manufacturer. The $IC_{50}$ values of the KDR kinase inhibition activity are calculated using XLfit software.

Assay Method:

(1) Dilution of the test compounds: each of the above three compounds is dissolved in DMSO to prepare a 10 µM stock solution and stored in –20° C. freezer. The stock solution is diluted to the four times concentration of the desired test concentration with 8% DMSO before use.

(2) 1.33× assay buffer: Dilute 5× assay buffer with distilled water into 1.33× assay buffer.

(3) Dilution of KDR kinase catalytic domain (KDR CD): Dilute KDR CD original stock with 1.33× assay buffer 10-fold. Aliquot into 5 µL/vial and store at –80° C. Repeated thaw and freezing should be avoided.

(4) Kinase/substrate mixture: add KDR CD stock and Tyr1 peptide in 1.33× assay buffer, to obtain mixture containing 0.6 ng/µL of KDR CD and 250-fold diluted Tyr1 peptide. Keep the mixture on ice until use.

(5) Mixture for control well C3: dilute phospho-peptide substrate in 1.33× assay buffer 250-fold. Mix carefully and keep on ice.

(6) ATP solution: Dilute 10 mM ATP stock solution in distilled water 250-fold. 40 µM of ATP solution is obtained and aliquoted into 100 µL/vial and stored at –20° C.

(7) Kinase inhibition: Add the following components in turn in a 384-well plate. Duplicated wells are tested for each concentration of each test compound and average value is used for calculation.

a) Add 2.5 µL of diluted test compound solution obtained from step (1) into all wells except for the control wells C1, C2 and C3. Add 2.5 µL of 8% DMSO instead of the test compound solution in control well C1, C2, C3.

b) Add 5 µL of kinase-substrate mixture obtained from step (4) into all wells, including control wells C1 and C2, but not C3. 5 µL of C3 mixture derived from step (5) is added into the control well C3.

c) Add 2.5 µL of 40 µM ATP solution obtained from step (6) into all wells including control well C2 but not C1 and C3. 2.5 µL of 1.33× assay buffer is added in control wells C1 and C3 instead of the ATP solution.

d) The plate is briefly centrifuged at 1000 rpm to make all reaction components sediment into the well. Seal the plate with aluminum foil and allow the reaction to proceed at room temperature (25° C.) for 1 hour on the shaker (250 rpm).

e) Dilution of enhancer solution (right before use): according to the recommendation of manufacturer, dilute enhancer stock with development dilution buffer 128-fold.

f) Fluorescence enhancement: add 5 µL/well of the diluted enhancer solution in all wells, briefly spin at 1000 rpm, re-seal the plate and let the reaction proceed at room temperature for an additional hour on the shaker.

g) Add 5 µL/well of stop solution to all wells, briefly spin at 1000 rpm. Mix at room temperature for 2 minutes on the shaker, and read florescence signals on Victor3 (Perkin Elmer) at excitation 400 nm, emission 445 nm/530 nm.

Calculation of KDR kinase inhibition activity:

(1) Calculation of ER (Emission Ratio):

$$\text{Emission Ratio} = \frac{\text{Coumarin Emission (445 nm)}}{\text{Fluorescein Emission (520 nm)}}$$

(2) Calculation of Phosphorylation Rate (%)

$$\% \text{ Phosphonylation} = 1 - \frac{(\text{Emission Ratio} \times F_{100\%}) - C_{100\%}}{(C_{0\%} - C_{100}) + [\text{Emission Ratio} \times (F_{100\%} - F_{0\%})]}$$

wherein:

Emission Ratio=Coumarin/Fluorescein ratio of sample wells $C_{100\%}$=Average Coumarin emission signal of the 100% Phos. Control (C3, 445 nm)

$C_{0\%}$=Average Coumarin emission signal of the 0% Phos. Control (C1, 445 nm)

$F_{100\%}$=Average Fluorescein emission signal of the 100% Phos. Control (C3, 520 nm)

$F_{0\%}$=Average Fluorescein emission signal of the 0% Phos. Control (C1, 520 nm)

Based on above assay conditions, the KDR kinase inhibition activity of the compounds of Formula A, B and C are determined.

Results: The KDR kinase inhibition activity $IC_{50}$s for compounds of Formula A, B, C are 0.021 µM, 0.038 µM and 0.111 µM, respectively.

Example 3

In Vitro Studies of FGFR1 Kinase Inhibition Activity

The Transcreener FP technology of Bellbrook Labs is used in the FGFR1 kinase activity assay. The kinase reaction was done in 96-well half area black plate (Greiner, Cat. 675076).

In each well, were added 5 μL of test compounds in 5% DMSO, 10 μL of 0.3 ng/μL FGFR1 kinase (Invitrogen, PV3146) diluted in assay buffer. The reaction was started by the addition of 10 μL of 62.5 ng/μL poly (Glu:Tyr, 4:1) substrate (Sigma, P0275) and 25 μmol/L of ATP mixture, and incubated for 60 minutes at room temperature. The final conditions for kinase assay were: 10 μM of ATP, 0.12 ng/μL of FGFR1 kinase, 25 ng/μL of substrate, 53.6 mmol/L of HEPES (pH 7.5), 21.6 mmol/L of $MgCl_2$, 0.536 mmol/L of $MnCl_2$, 1 mmol/L of DTT and 0.01% Triton X-100, 1% DMSO.

At the same time, an ADP standard curve was performed. The standard curve mimics a kinase reaction in the absence of test compound, kinase, and lipid substrate. The standard curve contained 12 concentration points, and total [ATP+ADP] ranged from 10 μM to 0.01 μM. 5 μL of 5% DMSO and 10 μL of assay buffer were added instead of test compound and FGFR1 kinase, respectively. Other conditions were the same as described above.

After reacting for 60 minutes at room temperature, 25 μL of transcreener Kinase Kit reagent—ADP Detection Mix—(Bellbrook Labs) was added and reacted for an additional 1.0 hours. The plates were then read in Tecan Infinite F500 at an excitation of 610 nm and an emission of 670 nm. The standard curve was created using Origin 8.0 software. The inhibition of test compound on ADP production was calculated based on ADP concentration calculated from standard curve. $IC_{50}$ was obtained using XLfit 2.0 software.

Results

| Compound | IC50 (μM) |
| --- | --- |
| compound of Formula A | 0.053 |

Example 4 hERG Assay 4.1 Cell Culture

A CHO cell line stably transfected with hERG cDNA and expressing hERG channels was used for the study. Cells were cultured in a medium comprising:
Dulbecco's Modified Eagle Medium (DMEM/F12)
10% (v/v) heat inactivated Fetal bovine serum (FBS)
1% (v/v) penicillin/streptomycin
500 μg/ml Geneticin® reagent (G418)

Before testing, cells were harvested using an Accumax (Innovative Cell Technologies).

For the electrophysiological recordings, the following solutions were used.

4.2 Solution

TABLE

Composition of internal and external solutions used in hERG patch clamp studies

| Reagent | External Solution (mM) | Internal Solution (mM) |
| --- | --- | --- |
| $CaCl_2$ | 1.8 | — |
| $MgCl_2$ | 1.0 | 1 |
| KCl | 4 | 130 |
| NaCl | 137 | — |
| Glucose | 10 | — |
| HEPES | 10 | 10 |
| EGTA | — | 5 |
| ATP | — | 5 |
| pH | 7.4 (adjusted with NaOH), Osmolarity ~280 mOsm | 7.25 (adjusted with KOH), osmolarity ~280 mOsm |

4.3 Recording System

Whole-cell recording was performed using a 700B (Axon Instruments). The cells were voltage clamped at a holding potential of −80 mV. The hERG current was activated by depolarizing at +20 mV for 2 sec, after which the current was taken back to −50 mV for 2 sec to remove the inactivation and observe the deactivating tail current. The first step at −50 mV was used as a baseline for measuring the tail current peak amplitude.

4.4 Compound Handling and Dilutions

Test compound was prepared as a 10 mM DMSO stock solution in a glass vial. The stock solution was mixed vigorously for 10 minute at room temperature. The stock solution was diluted in a glass vial using External Solution; the dilution was prepared no longer than 30 minutes before use. Equal amounts of DMSO (0.1%) were present at final dilution.

4.5 Electrophysiology Procedures

After achieving whole-cell configuration, the cells were monitored for 90 sec to assess stability and washed with external solution for 66 sec. The voltage protocol described above was then applied to the cells every 20 sec throughout the whole procedure. Only stable cells with recording parameters above threshold were allowed to enter the compound testing procedure.

External solution containing 0.1% DMSO (vehicle) was applied to the cells to establish the baseline. After allowing the current to stabilize for 3 minutes, the test compound was applied. The test compound solution was added in 4 steps and the cells were kept in the test solution until the compound's effect reached a steady state or for a maximum of 6 min. Subsequently, the positive control (10 nM Cisapride) was added. Washout with external solution was performed until the recovery of the current reached a steady state.

4.6 Data Analysis

Data were analyzed using Clampfit (both by Axon Instruments) and Origin 7 (Originlab Corporation).

The compound of Formula C inhibited hERG currents with an IC50 of 0.547 uM, while the compound of Formula A inhibited hERG with an IC50 of 6.8 uM.

Example 5

Pharmacokinetics (PK) Study

Experimental Method: The pharmacokinetics of the test compounds were studied with male ICR mice (n=6 for each group, weight 20-30 g) after a single intravenous (i.v.) and oral (p.o.) dosing at 2.5 and 10 mg/kg, respectively. For i.v. dosing formulation, the test compound was dissolved in DMSO (0.25%)-solutol (10%)-ethanol (10%)-physiological saline (79.75%) at the concentration of 0.25 mg/mL. And the p.o. dosing formulation (1 mg/mL) was prepared with 0.5% CMC-Na. After L v. or p.o. dosing, blood samples were collected via the ophthalmic vein at 0 (pre-dose), 5, 15, 30 min and 1, 1.5, 2, 4, 8, 24 h, anti-coagulated with heparin-Na.

After centrifugation, plasma samples were separated and protein precipitated with acetonitrile (containing internal standard). The concentration of the testing compounds in these plasma samples were then determined by LC/MS/MS.

Results: After oral dosing of 10 mg/kg, the AUC and Cmax of Compound B were 26 ng/mL·h and 20 ng/mL, respectively. At the same oral dose (10 mg/kg), the AUC and Cmax of Compound A were 397 ng/mL·h and 138 ng/mL, respectively. As can be seen, the compound of Formula A showed much higher plasma exposures, such as higher AUC and Cmax, than Compound B after oral administration in the mouse The following examples 6-10 show different processes for the preparation of Form I N-(2-(dimethylamino)ethyl)-1-(3-((4-((2-methyl-1H-indol-5-yl)oxy)pyrimidin-2-yl)amino)phenyl)methane sulfonamide.

Preparation of Form I N-(2-(dimethylamino)ethyl)-1-(3-((4-((2-methyl-1H-indol-5-yl)oxy)pyrimidin-2-yl)amino)phenyl)methanesulfonamide Example 6

The compound of Formula A (151 mg) was dissolved in 3 mL of ethanol with heating and stirring. The solution was hot filtered to remove insoluble particles. The filtrate was heated for another 5 minutes to obtain clear solution and then slowly cooled to room temperature with stirring. At room temperature, the mixture was stirred for an additional 4 hr at a medium stirring rate (100 rpm). The precipitates were collected by filtration and dried at 60° C. for 2 hrs under vacuum, to afford a white crystalline powder (Form I, 136 mg), mp (DSC): 166.6-168.2° C.

The powder X-ray diffractogram of the Form I obtained is shown in FIG. 1. It has peaks (2θ) chosen from those having about the following values: 7.1, 8.0, 8.7, 11.1, 11.8, each of the diffraction angles being ±0.2 degrees (2θ), wherein characteristic peaks (2θ) are identified as 7.1, 8.0 and 8.7.

DSC testing showed that the melting range of the Form I obtained was 166.6-168.2° C.

Example 7

The compound of Formula A (152 mg) was dissolved in 3 mL of acetonitrile with heating and stirring. Agitation and heating were continued until full dissolution was obtained. The insoluble particles were removed by hot filtration. The filtrate was refluxed for 5 minutes to obtain a clear solution, and then left to cool to room temperature on its own with stirring at medium stirring rate (100 rpm).

After the suspension was stirred for another 2 hours, the precipitates were collected by filtration and dried at 60° C. in vacuum oven for 4 hours to give the Form I product (113 mg, yield 74.3%).

The powder X-ray diffractogram is essentially the same as that of the Form I obtained in Example 5.

Example 8

The compound of Formula A (141.8 mg) was dissolved in 8 mL of toluene with heating and stirring. The stirring and heating were continued until full dissolution was obtained. It was then left to cool to room temperature on its own with stirring at a medium stirring rate (100 rpm). After the suspension was stirred for another 2 hours, the precipitates were collected by filtration and dried at 60° C. in a vacuum oven for 4 hours to give the Form I product (86 mg).

The powder X-ray diffractogram is essentially the same as that of the Form I product obtained in Example 5.

Example 9

Compound A (150 mg) was dissolved in 2.5 mL of acetone with heating and stirring. The insoluble particles were removed by hot filtration. The filtrate was refluxed for 5 minutes to obtain a clear solution. Then to the solution, 2.5 mL of water was added. After the addition, the solution was left to cool down to room temperature on its own with stirring at medium stirring rate (100 rpm).

The suspension was stirred for 4 hours. The precipitates were collected by filtration and dried at 60° C. in a vacuum oven to give the Form I product (123 mg). Melting point (measured by DSC): 165.6-167.5° C.

The powder X-ray diffractogram of this product is essentially the same as that of the Form I product obtained in Example 5.

Example 10

Compound A (180.3 mg) was dissolved in 6.0 mL of methanol with heating and stirring. Agitation and heating were continued until a full dissolution was obtained. The insoluble particles were removed by hot filtration. The filtrate was refluxed for 5 minutes to obtain a clear solution. To this solution, heptane (6.0 mL) was slowly added. After the addition, the mixture was concentrated until the final volume of 10 mL and then cooled to room temperature on its own accord.

The precipitates were collected by filtration and dried at 60° C. in vacuum oven to give the Form I product (118 mg).

The powder X-ray diffractogram is essentially the same as that of the Form I obtained in Example 6.

The following examples 11-12 show different processes for the preparation of Form II N-(2-(dimethylamino)ethyl)-1-(3-((4-((2-methyl-1H-indol-5-yl)oxy)pyrimidin-2-yl)amino)phenyl)methane sulfonamide Preparation of Form II N-(2-(dimethylamino)ethyl)-1-(3-((4-((2-methyl-1H-indol-5-yl)oxy)pyrimidin-2-yl)amino)phenyl)methane sulfonamide Example 11

Compound A (2.4 g) was dissolved in 35 ml of acetone with heating and stirring. Agitation and heating were continued until a full dissolution was obtained. The insoluble particles were removed by hot filtration. The filtrate was refluxed for 5 minutes to obtain a clear solution. Heptane (20 mL) was then added to the solution with stirring. After the completion of the addition, it was quickly cooled to 0-5° C. with stirring. At this temperature, the mixture was stirred for another 4 hours.

The precipitates were collected by filtration and dried at 60° C. for 2 hrs in a vacuum oven to give the Form II product (2.0 g, yield 83.3%), mp (DSC): 160.3-161.6° C.

The powder X-ray diffractogram of the Form II obtained is shown in FIG. 5. It has peaks (2θ) chosen from those having about the following values: 6.8, 9.8, 10.5, 10.7, 13.6, 15.0, each of the diffraction angles being ±0.2 degrees (2θ), wherein characteristic peaks (2θ) are identified as 6.8, 9.8, 10.5, and 10.7.

Example 12

Compound A (17 g) was dissolved in 425 mL of ethanol with heating and stirring. Agitation and heating were continued until full dissolution was achieved. The insoluble particles were removed by hot filtration. The filtrate was refluxed for 5 minutes to obtain a clear solution. The solution was cooled to 50° C. and was added with, 0.34 g (2% w/w) of Form II seeds. After the addition, the solution was left to cool down to room temperature on its own accord. The mixture was stirred for another 4 hr at the room temperature and the precipitates were collected by filtration, dried at 60° C. in vacuum oven to give 15 g of product of crystal Form II, yield 88.0%.

The powder X-ray diffractogram was essentially the same as that of the Form II product obtained in Example 11.

DSC measurement showed the onset temperature of the Form II obtained was at 160.3° C., and a peak appeared at 161.6° C.

Example 13

Hygroscopicity Studies of Form I and From II N-(2-(dimethylamino)ethyl)-1-(3-((4-((2-methyl-1H-indol-5-yl)oxy)pyrimidin-2-yl)amino)phenyl)methanesulfonamide Hygroscopicity of the Form I and From II products were tested with saturated salt solution method.

About 1 g of the Form I and Form II samples were accurately weighted respectively, and the samples were put into a desiccator containing saturated NaCl solution. The desiccator was closed and left standing for 10 days at 25° C. Then the samples were taken out and weighed again, and the weight gain was calculated.

| material | 0 day Form | 10 days Form | Weight gained (% w/w) |
|---|---|---|---|
| Form I sample | I | I | <0.1% |
| Form II sample | II | II | <1% |

The Form I sample was found to be non-hygroscopic, and its weight gain under 92.5% RH was less than 0.1%. The Form II sample was found slightly hygroscopic with less than 1% weight gain. The Form I and Form II samples after testing were analyzed by an X-ray diffractometer and the diffractograms were found comparable to those of FIG. 1 and FIG. 5 respectively.

The hygroscopicity test results indicated that both the Form I and the Form II are stable under the testing humidity conditions, and the slight surface absorption of moisture does not change the crystalline forms. And hence both the Form I and Form II can be used in pharmaceutical product for the applications as described herein.

Example 14

Thermodynamic Stability Comparison

A suspension of the Form I and the Form II mixture in methanol was stirred at 60° C. for 20 h. Then the suspension was filtered with a Buchner funnel and paper disk, and dried under a vacuum oven. The dried sample was then analyzed by powder X-ray diffraction, and the diffractogram was found comparable to that of FIG. 1.

Characteristic diffraction peaks of the Form II were not found in the obtained X-ray diffractogram, indicating that Form II in the suspension was transformed to the Form I during the slurry process, and Form I was physically and/or thermodynamically more stable than Form II under the transforming conditions.

Form I thus can also be prepared by the transformation of the Form II in suitable solvents.

Results:

Form I is stable both under high humidity conditions and in recrystallization solvents, and can be prepared on an industrial scale, Form II can be used as an intermediate for preparing the Form I, which can be used as a suitable solid state crystalline form in a pharmaceutical dosage. And Form II also can be used in pharmaceutical dosage due to its good stability.

What is claimed is:

1. N-(2-(dimethylamino)ethyl)-1-(3-((4-((2-methyl-1H-indol-5-yl)oxy)pyrimidin-2-yl)amino)phenyl)methanesulfonamide,

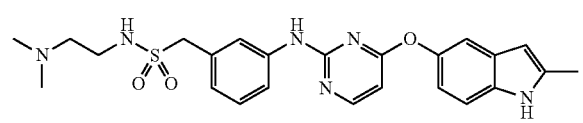

and/or a pharmaceutically acceptable salt thereof.

2. A pharmaceutical composition, comprising at least one pharmaceutically acceptable carrier and N-(2-(dimethylamino)ethyl)-1-(3-((4-((2-methyl-1H-indol-5-yl)oxy)pyrimidin-2-yl)amino)phenyl)methanesulfonamide,

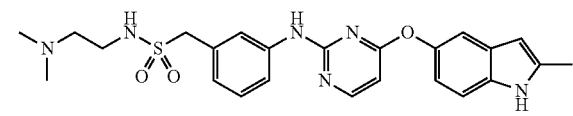

and/or a pharmaceutically acceptable salt thereof.

3. Form I N-(2-(dimethylamino)ethyl)-1-(3-((4-((2-methyl-1H-indol-5-yl)oxy)pyrimidin-2-yl)amino)phenyl)methanesulfonamide.

4. Form I N-(2-(dimethylamino) ethyl)-1-(3-((4-((2-methyl-1H-indol-5-yl)oxy)pyrimidin-2-yl)amino)phenyl)methanesulfonamide substantially free of the amorphous form N-(2-(dimethylamino) ethyl)-1-(3-((4-((2-methyl-1H-indol-5-yl)oxy)pyrimidin-2-yl)amino)phenyl)methanesulfonamide and also substantially free of Form II N-(2-(dimethylamino) ethyl)-1-(3-((4-((2-methyl-1H-indol-5-yl)oxy)pyrimidin-2-yl)amino)phenyl)methanesulfonamide.

5. A method of preparing Form I N-(2-(dimethylamino) ethyl)-1-(3-((4-((2-methyl-1H-indol-5-yl)oxy)pyrimidin-2-yl)amino)phenyl)methanesulfonamide, comprising:
  (1) mixing N-(2-(dimethylamino)ethyl)-1-(3-((4-((2-methyl-1H-indol-5-yl)oxy)pyrimidin-2-yl)amino)phenyl)methanesulfonamide with at least one dissolution organic solvent, then heating the mixture to reflux to obtain a solution;
  (2) cooling the solution to ambient temperature; and
  (3) isolating Form I N-(2-(dimethylamino)ethyl)-1-(3-((4-((2-methyl-1H-indol-5-yl)oxy)pyrimidin-2-yl)amino) phenyl)methanesulfonamide.

6. The method of claim 5, wherein the at least one dissolution organic solvent is chosen from alcohols and aprotic solvents.

7. The method of claim 6, wherein the alcohols are chosen from methanol, ethanol, and isopropanol.

8. The method of claim 6, wherein the aprotic solvents are chosen from acetone, acetonitrile, ethyl acetate, toluene, dichloromethane, and N,N-dimethylformamide.

9. A method of preparing Form I N-(2-(dimethylamino)ethyl)-1-(3-((4-((2-methyl-1H-indol-5-yl)oxy)pyrimidin-2-yl)amino)phenyl)methanesulfonamide, comprising:
   (1) mixing N-(2-(dimethylamino)ethyl)-1-(3-((4-((2-methyl-1H-indol-5-yl)oxy)pyrimidin-2-yl)amino)phenyl)methanesulfonamide with at least one dissolution solvent, then heating the mixture to reflux to obtain a first solution;
   (2) adding at least one anti-dissolution organic solvent to the first solution at refluxing temperature to obtain a second solution;
   (3) leaving the second solution to cool at ambient temperature; and
   (4) isolating Form I N-(2-(dimethylamino)ethyl)-1-(3-((4-((2-methyl-1H-indol-5-yl)oxy)pyrimidin-2-yl)amino)phenyl)methanesulfonamide.

10. The method of claim 9, wherein the at least one dissolution solvent is chosen from methanol, ethanol, acetone, acetonitrile, and N,N-dimethylformamide.

11. The method of claim 9, wherein the at least one anti-dissolution solvent is chosen from water, heptane, hexane, and ethyl acetate.

12. The method of claim 9, wherein the volume ratio of the at least one dissolution solvent to the at least one anti-dissolution solvent ranges from 1:3 to 5:1.

13. A pharmaceutical composition, comprising at least one pharmaceutically acceptable carrier and Form I N-(2-(dimethylamino)ethyl)-1-(3-((4-((2-methyl-1H-indol-5-yl)oxy)pyrimidin-2-yl)amino)phenyl)methanesulfonamide.

14. Form II N-(2-(dimethylamino)ethyl)-1-(3-((4-((2-methyl-1H-indol-5-yl)oxy)pyrimidin-2-yl)amino)phenyl)methanesulfonamide.

15. Form II N-(2-(dimethylamino) ethyl)-1-(3-((4-((2-methyl-1H-indol-5-yl)oxy)pyrimidin-2-yl)amino)phenyl)methanesulfonamide substantially free of the amorphous form N-(2-(dimethylamino)ethyl)-1-(3-((4-((2-methyl-1H-indol-5-yl)oxy)pyrimidin-2-yl)amino)phenyl)methanesulfonamide and also substantially free of Form I N-(2-(dimethylamino) ethyl)-1-(3-((4-((2-methyl-1H-indol-5-yl)oxy)pyrimidin-2-yl)amino)phenyl)methanesulfonamide.

16. A method of preparing Form II N-(2-(dimethylamino)ethyl)-1-(3-((4-((2-methyl-1H-indol-5-yl)oxy)pyrimidin-2-yl)amino)phenyl)methanesulfonamide, comprising:
   (1) mixing N-(2-(dimethylamino)ethyl)-1-(3-((4-((2-methyl-1H-indol-5-yl)oxy)pyrimidin-2-yl)amino)phenyl)methanesulfonamide with at least one dissolution solvent, and heating the mixture to reflux to obtain a first solution;
   (2) adding at least one anti-dissolution solvent to the first solution at reflux temperature to obtain a second solution;
   (3) cooling the second solution to 0-5° C. at a cooling rate of 1-40° C./minute; and
   (4) isolating Form II N-(2-(dimethylamino)ethyl)-1-(3-((4-((2-methyl-1H-indol-5-yl)oxy)pyrimidin-2-yl)amino)phenyl)methanesulfonamide.

17. The method of claim 16, wherein the at least one dissolution solvent is chosen from alcohols and aprotic solvents.

18. The method of claim 17, wherein the alcohols are chosen from methanol, and ethanol.

19. The method of claim 17, wherein the aprotic solvents are chosen from acetone, acetonitrile, ethyl acetate, toluene, dichloromethane, and N,N-dimethylformamide.

20. A method of preparing Form II N-(2-(dimethylamino)ethyl)-1-(3-((4-((2-methyl-1H-indol-5-yl)oxy)pyrimidin-2-yl)amino)phenyl)methanesulfonamide, comprising:
   (1) mixing N-(2-(dimethylamino)ethyl)-1-(3-((4-((2-methyl-1H-indol-5-yl)oxy)pyrimidin-2-yl)amino)phenyl)methanesulfonamide with at least one dissolution solvent, and heating the mixture to reflux to obtain a solution;
   (2) cooling the solution, then seeding said cooled solution with Form II;
   (3) cooling said seeded solution to ambient temperature, and
   (4) isolating Form II N-(2-(dimethylamino)ethyl)-1-(3-((4-((2-methyl-1H-indol-5-yl)oxy)pyrimidin-2-yl)amino)phenyl)methanesulfonamide.

21. The method of claim 20, wherein the solution in (2) is slowly cooled to 45-55° C.

22. The method of claim 20, wherein the seeded solution is slowly cooled to ambient temperature.

23. The method of claim 20, wherein the at least one dissolution solvent is chosen from alcohols and aprotic solvents.

24. The method of claim 23, wherein the alcohols are chosen from methanol and ethanol.

25. The method of claim 23, wherein the aprotic solvents are chosen from acetone, acetonitrile, ethyl acetate, toluene, dichloromethane, and N,N-dimethylformamide.

26. A pharmaceutical composition, comprising at least one pharmaceutically acceptable carrier and Form II N-(2-(dimethylamino)ethyl)-1-(3-((4-((2-methyl-1H-indol-5-yl)oxy)pyrimidin-2-yl)amino)phenyl)methanesulfonamide.

* * * * *

UNITED STATES PATENT AND TRADEMARK OFFICE
CERTIFICATE OF CORRECTION

| | |
|---|---|
| PATENT NO. | : 8,658,658 B2 |
| APPLICATION NO. | : 13/510249 |
| DATED | : February 25, 2014 |
| INVENTOR(S) | : Su et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 64 days.

Signed and Sealed this
Eleventh Day of August, 2015

Michelle K. Lee
*Director of the United States Patent and Trademark Office*